(12) United States Patent
Shaikh et al.

(10) Patent No.: US 10,024,864 B2
(45) Date of Patent: Jul. 17, 2018

(54) FUNCTIONALIZED GOLD NANOPARTICLES AND METHODS THEREOF

(71) Applicant: KING FAHD UNIVERSITY OF PETROLEUM AND MINERALS, Dhahran (SA)

(72) Inventors: Mohammed Nasiruzzaman Shaikh, Kolkata (IN); Aasif Helal, Kolkata (IN); Abiola Azeez Jimoh, Oledo (NG)

(73) Assignee: King Fahd University of Petroleum and Minerals, Dhahran (SA)

(*) Notice: Subject to any disclaimer, the term of this patent is extended or adjusted under 35 U.S.C. 154(b) by 286 days.

(21) Appl. No.: 14/937,499

(22) Filed: Nov. 10, 2015

(65) Prior Publication Data

US 2017/0131286 A1 May 11, 2017

(51) Int. Cl.
*G01N 21/64* (2006.01)
*G01N 33/553* (2006.01)
(Continued)

(52) U.S. Cl.
CPC ........... *G01N 33/587* (2013.01); *C07F 1/005* (2013.01); *G01N 21/643* (2013.01); *G01N 21/6428* (2013.01); *G01N 33/54346* (2013.01); *G01N 33/553* (2013.01); *G01N 33/84* (2013.01); *G01N 2800/04* (2013.01)

(58) Field of Classification Search
CPC ............... C07F 1/005; G01N 2800/04; G01N 33/54346; G01N 33/553; G01N 33/587; G01N 33/84; G01N 33/20; G01N 21/64; G01N 21/6428; G01N 21/643; G01N 21/6486; Y10T 436/17; Y10T 436/173845; Y10T 436/18; Y10T 436/182; Y10T 436/203332

USPC ......... 436/73, 79, 80, 81, 84, 106, 111, 119, 436/120, 131, 163, 164, 172; 422/82.05, 422/82.08
See application file for complete search history.

(56) References Cited

U.S. PATENT DOCUMENTS

2003/0109056 A1* 6/2003 Vossmeyer ............ G01N 21/77
436/169
2010/0068817 A1* 3/2010 Mirkin ................. C12Q 1/6813
436/80

(Continued)

OTHER PUBLICATIONS

Mayer et al. European Journal of Inorganic Chemistry, 2008, pp. 3614-3623.*
Md., Nasiruzzaman S., et al., "Gold Nanoparticles Coated with Gd-Chelate as a Potential CT/MRI Bimodal Contrast Agent", Bulletin of the Korean Chemical Society, vol. 31, No. 5, pp. 1177-1181, (2010).

(Continued)

*Primary Examiner* — Maureen Wallenhorst
(74) *Attorney, Agent, or Firm* — Oblon, McClelland, Maier & Neustadt, L.L.P.

(57) ABSTRACT

Gold nanoparticles functionalized with thiolated, bidentate Schiff base ligands. The Schiff base ligands form a ligand monolayer surrounding and binding to the surface of a gold nanoparticle core through Au—S linkages. The functionalized gold nanoparticle composites have a spherical shape, an average diameter of 7-15 nm and a narrow particle size distribution. Methods of assessing these functionalized gold nanoparticle composites as fluorescent probes in Fe(III) chemosensing applications, methods of preparing the functionalized gold nanoparticle composites and methods of detecting Fe(III) ions with the same are also provided.

19 Claims, 7 Drawing Sheets

(51) Int. Cl.
  *G01N 33/58* (2006.01)
  *C07F 1/00* (2006.01)
  *G01N 33/543* (2006.01)
  *G01N 33/84* (2006.01)

(56) References Cited

U.S. PATENT DOCUMENTS

2012/0225021 A1* 9/2012 Qian .................... G01N 21/64
                                                           424/9.6
2015/0037585 A1   2/2015 Compel et al.
2015/0353580 A1* 12/2015 Hutchison ............... C07F 1/005
                                                           436/164

OTHER PUBLICATIONS

Wang, Shasha, et al., "Highly Sensitive Fluorescence Detection of Copper Ion Based on its Catalytic Oxidation to Cysteine Indicated by Fluorescein Isothiocyanate Functionalized Gold Nanoparticles", URL: http://www.sciencedirect.com/science/article/pii/S0927775714009790, Colloids and Surfaces A: Physicochemical and Engineering Aspects, vol. 468, pp. 333-338, (2015).

D, Tan, et al., "Aptamer Functionalized Gold Nanoparticles Based Fluorescent Probe for the Detection of Mercury (II) Ion in Aqueous Solution.", URL: http://www.ncbi.nlm.nih.gov/pubmed/23708619, TALANTA, 1 Page, (2013) (Abstract only).

* cited by examiner

FUNCTIONALIZED GOLD NANOPARTICLES AND METHODS THEREOF

STATEMENT OF FUNDING ACKNOWLEDGEMENT

This project was funded by the National Plan for Science, Technology and Innovation (MAARIFAH)—King Abdulaziz City for Science and Technology—the Kingdom of Saudi Arabia, award number (12-NAN2389-04).

BACKGROUND OF THE INVENTION

Technical Field

The present invention relates to modified and functionalized gold nanoparticles. More particularly, the present invention relates to gold nanoparticles coated with Schiff-base function groups. The present invention includes the use of the gold nanoparticles as fluorescent probes for chemical sensing of metal ions such as Fe(III).

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Iron with its chemical versatility is essential for the proper functioning of numerous organisms in the entire spectrum of biological system. In human body, iron is one of the most essential trace elements; deficiency of ferric ion (Fe (III)) in the body causes anemia, hemochromatosis, liver damage, diabetes, Parkinson's disease and cancer [B. D'Autreáux, N. P. Tucker, R. Dixon and S. A. Spiro, Nature 2005, 437, 769-772; Y. Xing and A. Ton, Org. Lett 2006, 8, 1549; G. E. Tumambac, C. M. Rosencrance and C. Wolf, Tetrahedron 2004, 60, 11293; S. Narayanaswamy, T. Govindaraju, Sens. Actuators B 2012, 161, 304—each incorporated herein by reference in its entirety]. Fe(III) also plays crucial role in the growth and development of living cells and catalyze numerous biochemicals processes [J. W. Lee and J. D. Helmann. Nature 2006, 440, 363-367—incorporated herein by reference in its entirety]. On the other hand, the physiological abundance of Fe(III) causes imbalance, thereby triggering multiple organ (heart, pancreas, and liver) failure [E. D. Weinberg, Eur J Cancer Prev 1996, 5, 19-36; Z. Li, Y. Zhou, K. Yin, Z. Yu, Y. Li, J. Ren, Dyes and Pigments 2014 105, 7-11—each incorporated herein by reference in its entirety]. Therefore, detection of Fe(III) in trace levels is of great relevance. In this regard, judicious selection and proper design of an adequate receptor is vital. Recently, a number of studies on the development of Schiff-base based chemosensors for the detection of Hg(II), Zn(II), Al(III) and other ions have been reported in literature [S. A. Lee, G. R. You, Y. W. Choi, H. Y. Jo, A. R. Kim, I. Noh, S.-J. Kim, Y. Kim, and C. Kim, Dalton Trans., 2014, 43, 6650-6659; Y. Zhou, H. N. Kim, J. Yoon, Bioorg. Med. Chem. Lett. 2010, 20, 125-128; Z. Dong, X. Tian, Y. Chen, Y. Guo, J. Ma, RSC Adv. 2013, 3, 1082-1088—each incorporated herein by reference in its entirety]. However, the availability of chemosensors for Fe(III) with high detection threshold is rather limited.

Conventional Fe(III) detection and analytical techniques include, for example, coupled-plasma atomic emission spectrometry (ICP-AES), inductively coupled plasma mass spectrometry (ICPMS), atomic absorption spectrometry (AAS) and voltammetry [K. Pomazal, C. Prohaska, I. Steffan, G. Reich, J. F. K. Huber, Analyst, 1999, 124, 657; M. E. C. Busto, M. M. Bayon, E. B. Gonzalez, J. Meija, A. S. Medel, Anal. Chem., 2005, 77, 5615; G. L. Arnold, S. Weyer, A. D. Anbar, Anal. Chem., 2004, 76, 322; J. E. T. Andersen, Analyst, 2005, 130, 385; C. M. G. van den Berg, Anal. Chem., 2006, 78, 156—each incorporated herein by reference in its entirety]. However, these methods are expensive, bulky and time consuming, as they require tedious pretreatment procedures for sample preparation. Fluorescent microscopy based on optical fluorescence on the other hand, is a simple and easy, low cost and highly selective tool for studying localization, trafficking and expression levels of biomolecules and metal ions within living cells [O. Tour, S. Adams, R. Kerr, R. Meijer, T. Sejnowski, R. Tsien, R. Y. Tsien, Nat. Chem. Biol., 2007, 3, 423-431; (b) M. Hangauer, C. Bertozzi, Angew. Chem., Int. Ed., 2008, 47, 2394-2397—incorporated herein by reference in its entirety]. To date, most of the Fe(III) sensing is based either on the fluorescence quenching mechanism because of the paramagnetic nature of ferric iron, or on the "turn on" mechanism [J. L. Bricks, A. Kovalchuk, C. Trieflinger, M. Nofz, M. Buschel, A. I. Tolmachev, J. Daub, K. Rurack, J. Am. Chem. Soc. 127 (2005) 13522-13529; J. P. Sumner, R. Kopelman, Analyst 130 (2005) 528-533; M. Y. She, Z. Yang, B. Yin, J. Zhang, J. Gu, W. T. Yin, J. L. Li, G. F. Zhao, Z. Shi, Dyes Pigments 92 (2012) 1337-1343; S. R. Liu, S. P. Wu, Sensor. Actuat. B-Chem. 171 (2012) 1110-1116; M.-R. Huang, S.-J. Huang, X.-G. Li, J. Phys. Chem. C 115 (2011) 5301-5315—each incorporated herein by reference in its entirety].

Merging nanotechnology with the signaling unit can lead to the formation of unique materials, thereby enabling the development of a suite of highly efficient chemosensors for their niche applications in drug delivery, imaging, catalysis, chemical and biochemical sensing [M. N. Shaikh, H.-K. Kim, J-A. Park, Y. Chang and T.-J. Kim, Bull. Korean Chem. Soc. 2010, 31, 1177-1181; C. Alric, J. Taleb, G. L. Duc, C. Mandon, C. Bilotey, A. L. Meur-Herland, T. Brochard, F. Vocanson, M. Janier, P. Perriat, S. Roux and O. Tillement, J. Am. Chem. Soc. 2008, 130, 5908; R. Abu-Reziq, H. Alper, D. Wang and Michael L. Post, J. Am. Chem. Soc. 2006, 128, 5279-5282; J.-J. Lin, J.-S. Chen, S.-J. Huang, J.-H. Ko, Y.-M. Wang, T,-L. Chen, L.-F. Wang, Biomaterials 2009, 30, 5114-5124; L. Bai, L. Zhu, C. Y. Ang, X. Li, S. Wu, Y. Zeng, H. Agren and Y. Zhao, Chem. Eur. J. 2014, 20, 4032-4037—each incorporated herein by reference in its entirety]. Gold nanoparticles (AuNPs), for example, have found applications, on the basis of their size- and shape-controlled synthesis, ease of functionalization and facile surface modification with diverse ligands. In this context, considerable effort has been made for developing AuNPs as excellent probes for cations [S.-P. Wu, Y.-P. Chen, Y.-M. Sung, Analyst 2011, 136, 1887-1891; Y. Kim, R. C. Johnson, J. T. Hupp, Nano Lett. 1 (2001) 165-167; Y. Xue, H. Zhao, Z. Wu, X. Li, Y. He, Z. Yuan, Analyst 136 (2011) 3725-3730; J. Yin, T. Wu, J. Song, Q. Zhang, S. Liu, R. Xu, H. Duan, Chem. Mater. 23 (2011) 4756-4764; A.-J. Wang, H. Guo, M. Zhang, D.-L. Zhou, R.-Z. Wang, J.-J. Feng, Microchim. Acta180 (2013) 1051-1057; V. V. Kumar, S. P. Anthony, Sens. Actuators B 191 (2014) 31-36; S. K. Tripathy, J. Y. Woo, C. Han, Sens. Actuators B 181 (2013) 114-118; Y. Chen, I. Lee, Y. Sung, S. Wu, Sens. Actuators B 188 (2013) 354-359; D. Maity, R. Gupta, R. Gunupuru, D. N. Srivastava, P. Paul, Sens. Actuators B 191 (2014) 757-764—each incorporated herein by reference in its entirety], anions [K. S. Youk, K. M. Kim, A. Chatterjee, K. H. Aim, Tetrahedron Lett. 49 (2008) 3652-3655; W. L. Daniel, M. S. Han, J. S. Lee, C. A. Mirkin, J. Am. Chem. Soc. 131 (2009) 6362-6363; L. Chen, W. Lu, X. Wang, L. Chen, Sens. Actuators B 182 (2013) 482-488; H. Deng, C. Wu, A. Liu, G. Li, W. Chen, X. Lin, Sens. ActuatorsB 191 (2014) 479-484—each incorporated herein by reference in its entirety], small molecules [Z. Sun, Z. Cui, H. Li, Sens. Actuators B 183 (2013) 297-302—incorporated herein by reference in its entirety], proteins [C. S. Tsai, T. B. Yu, C. T. Chen, Chem. Commun. 427 (2005) 4273-4275; A. Laromaine, L. Koh, M. Murugesan, R. V. Ulijn, M. M. Stevens, J. Am. Chem. Soc. 129 (2007) 4156-4157—each incorporated herein by reference in its entirety], nucleic acids [H. Li, L. Rothberg, Proc. Natl. Acad. Sci. U.S.A. 101 (2004) 14036-14039; C. A. Mirkin, R. L. Letsinger, R. C. Mucic, J. J. Storhoff, Nature 382 (1996) 607-609—each incorporated herein by reference in its entirety], and, other analytes. Recently, Bai et al. have reported 4-piperazinyl-1, 8-naphthalimide functionalized AuNPs for Fe(III) recognition via interparticle aggregation. AuNPs can be modified by capping agents, possess excellent optical properties such as high extinction coefficients, and distance-dependent plasmonic absorption [M.-C. Daniel, D. Astruc, Chem. Rev. 104 (2004) 293-346; C. Burda, X. Chen, R. Narayanan, M. A. El-Sayed, Chem. Rev. 105 (2005) 1025-1102—each incorporated herein by reference in its entirety]. This has led to the development of functionalized AuNPs for application as colorimetric probes. Notably, they have received great attention in visual sensing because of measurable plasmonic absorbance shift [A. Majzik, L. Fülöp, E. Csapó, D. Seb"ok, T. Martinek, F. Bogár, B. Penke, Imre Dékány, Colloids Surf. B 81 (2010) 235-241; E. Csapó, R. Patakfalvi, V. Hornok, Á. Sipos, A. Szalai, M. Csete, I. Dékány, Colloids Surf. B 98 (2012) 43-49; A. Szalai, Á. Sipos, E. Csapó, L. Tóth, M. Csete, I. Dékány, Plasmonics 8 (2013) 53-62—each incorporated herein by reference in its entirety].

In contrast to the availability of such diverse chemosensors, organic ligand coated AuNP based sensors, such as DNA aptamer functionalized AuNPs [Tan D., He Y., Xing X., Zhao Y., Tang H., Pang D., Talanta. 113 (2013) 26-30—incorporated herein by reference in its entirety], have not been as frequently explored.

In view of the foregoing, one object of the present disclosure is to provide gold nanoparticle-based chemosensors with high selectivity and high detection threshold for metal ions such as Fe(III).

BRIEF SUMMARY OF THE INVENTION

According to a first aspect, the present disclosure provides a fluorescent gold nanoparticle composite comprising a gold nanoparticle core and a ligand monolayer surrounding the gold nanoparticle core. The ligand monolayer comprises a plurality of substituted or unsubstituted (E)-2-(((4-mercaptophenyl)imino)methyl) phenol units having Au—S linkages to the gold nanoparticle core.

In one or more embodiments, the ligand monolayer comprises 2-12 of (E)-2-(((4-mercaptophenyl)imino)methyl) phenol units.

In some embodiments, the fluorescent gold nanoparticle composite has a spherical shape and an average diameter of 7-15 nm.

In one or more embodiments, more than 75% of the particles of the fluorescent gold nanoparticle composite have a diameter of 8-10 nm.

In certain embodiments, each of the plurality of (E)-2-(((4-mercaptophenyl)imino)methyl) phenol units comprises an —ON— electron donor group.

In one embodiment, the —ON— electron donor group is formed by an imino nitrogen of an amine group of the (E)-2-(((4-mercaptophenyl)imino)methyl) phenol molecule and an oxygen of a deprotonated phenol ring of the (E)-2-(((4-mercaptophenyl)imino)methyl) phenol molecule.

In one or more embodiments, the fluorescent gold nanoparticle composite has two plasmonic absorption peaks at 345-355 nm and 530-540 nm.

In one or more embodiments, upon binding with one or more Fe(III) ions, a fluorescence signal emits at 490-495 nm and a plasmonic absorption peak shifts from 530-540 nm to 555-565 nm.

In one or more embodiments, the fluorescent gold nanoparticle composite has a Fe(III) binding constant of 8.2-8.7× $10^5$ $M^{-1}$ as calculated from absorption titration.

In one or more embodiments, the fluorescent gold nanoparticle composite has a Fe(III) binding constant of 2.5-3.0× $10^5$ $M^{-1}$ as calculated from emission titration.

According to a second aspect, the present disclosure provides a method for detecting and quantifying Fe(III) ions in a fluid sample. The method comprises contacting the fluid sample with the fluorescent gold nanoparticle composite in accordance with the first aspect of the invention and measuring fluorescence emission at 490-495 nm to determine Fe(III) concentration in the fluid sample. During the contacting, the fluorescent gold nanoparticle composite selectively binds to the Fe(III) ions at a Fe(III)/(E)-2-(((4-mercaptophenyl)imino)methyl) phenol molar ratio of 1:1, causing a reduction in the fluorescence emission.

In at least one embodiment, the selective binding of the fluorescent gold nanoparticle composite to the Fe(III) ions further causes a shift in a plasmonic absorption peak from 530-540 nm to 555-565 nm.

In some embodiments, the selective binding of the fluorescent gold nanoparticle composite to the Fe(III) ions further results in formation of an aggregate. In one embodiment, the method further comprises removing the aggregate from the fluid sample.

In one or more embodiments, the method further comprises measuring the fluorescence emission of a plurality of calibration samples to obtain a calibration curve. The plurality of calibration samples comprise different, known amounts of Fe(III) ions.

In at least one embodiment, the method is executed in batch mode or fixed mode.

In some embodiments, the fluorescent gold nanoparticle composite is present at a concentration of 5-25 μM.

In one or more embodiments, the method has a Fe(III) detection limit of 1.0-1.5 μM without interference from one or more of other metal ions.

In some embodiments, the one or more of other metal ions are selected from the group consisting of Al(III), Ni(II), Cu(II), Co(II), Hg(II), Zn(II), Na, K, Ca(II) and Rb.

In one or more embodiments, the fluid sample comprises 10-100% v/v of water as a solvent.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
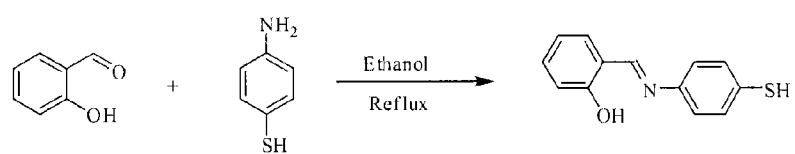
FIG. 1 is a schematic diagram illustrating the synthesis of a (E)-2-(((4-mercaptophenyl)imino)methyl) phenol thiolated Schiff base ligand for gold nanoparticles according to one embodiment.

Referring now to the drawings, wherein like reference numerals designate identical or corresponding parts throughout the several views.

The present disclosure relates to fluorescent gold nanoparticle composites, methods of preparing the same and methods of detecting and determining the amount of Fe(III) in a fluid sample with the gold nanoparticle composites.

Gold nanoparticles are modified or functionalized with a Schiff base compound or a derivative there. As used herein, a "Schiff base" refers to an organic compound of a general formula as shown below:

(Formula 1)

where $R_1$, $R_2$ and $R_3$ are alkyl or aryl groups. Hence, the Schiff base is a compound characterized by a functional group that contains a carbon-nitrogen double bond with the nitrogen atom connected to an aryl or alkyl group.

Specifically, a plurality of the Schiff base compounds act as ligands and are coordinated to a central core gold nanoparticle, thereby forming a monolayer of the Schiff base molecules surrounding and coating the gold nanoparticle. The ligand monolayer comprises 2 to 12 of the Schiff base molecules coordinated to the gold nanoparticle core, preferably 4 to 10, more preferably 4 to 8. In one embodiment, 6 of the Schiff base molecules are attached to the gold nanoparticle.

In at least one embodiment, the Schiff base ligand is (E)-2-(((4-mercaptophenyl)imino)methyl) phenol and is in accordance with Formula 2 as shown below.

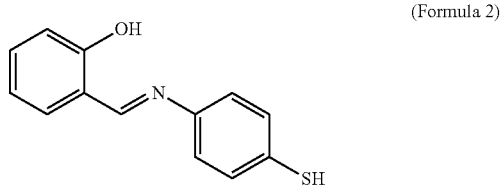 [SMILES: Oc1ccccc1/C=N/c1ccc(S)cc1]

(Formula 2)

As shown in Formula 2, the (E)-2-(((4-mercaptophenyl)imino)methyl) phenol Schiff base ligand is thiolated and bidentate, containing one phenol group (—OH) and one thiol group (—SH) as electron donor groups. The C=N imino group is linked to two aryl rings, each of which may be substituted by one or more substituent groups selected from the group consisting of a halogen group, a $C_1$-$C_6$ alkyl group, a $C_2$-$C_8$ alkenyl group, a $C_6$-$C_{24}$ aryl group, or a $C_1$-$C_6$ alkoxy group.

When bonded to the gold nanoparticle core, each of the (E)-2-(((4-mercaptophenyl)imino)methyl) phenol molecules in the ligand monolayer forms an Au—S linkage to the nanoparticle.

The gold nanoparticle composite comprising the gold nanoparticle core and the plurality of (E)-2-(((4-mercaptophenyl)imino)methyl) phenol ligands is of a spherical shape and has an average size (diameter) of 7-15 nm, preferably 7-12 nm, more preferably 8-10 nm. The nanoparticle size distribution is 5-30 nm, with more than 75% of the particles having a diameter in the range of 8-10 nm and more than 90% of the particles having a diameter in the range of 5-15 nm.

The molecular weight of the gold nanoparticle composite comprising the gold nanoparticle core and (E)-2-(((4-mercaptophenyl)imino)methyl) phenol ligands is 0.5-3.0 kDa, preferably 1.0-2.5 kDa, more preferably 1.5-2.0 kDa.

The (E)-2-(((4-mercaptophenyl)imino)methyl) phenol Schiff base can be prepared by refluxing equimolar amounts of salicylaldehyde and 4-aminothiophenol in ethanol at 85-100° C. for 4-8 h, preferably 5-7 h. Gold nanoparticles are then modified and functionalized by adding a minimal methanol solution of the thiolated, bidentate Schiff base ligand (5-20 mg/ml, preferably 6-15 mg/ml, more preferably 8-12 mg/ml) to a gold nanoparticle solution (uncoated or pre-coated with citrate ligands as stabilizing agents) at a ligand/nanoparticle volume ratio 1:50-200, preferably 1:75-150, more preferably 1:80-120. The gold nanoparticle-Schiff base ligand mixture is stirred for 4-8 h, preferably 5-7 h. A volume of acetone that is equal to the gold nanoparticle-Schiff base ligand mixture is then added to the mixture and the stirring is continued for another 2-6 h, preferably 3-5 h. The gold nanoparticle composites are precipitated at the end of the stirring session and can be collected by centrifugation.

All of the synthesis steps are preferably carried out under at inert atmosphere using the Schlenk line (vacuum gas manifold).

The binding of one or more of (E)-2-(((4-mercaptophenyl)imino)methyl) phenol molecules to a core gold nanoparticle causes a visible absorption band shift ($\lambda_{max}$) from 500-515 nm (uncoated gold nanoparticle) or 515-525 nm (gold nanoparticle pre-coated with citrate ligands) to 530-540 nm. Moreover, there is an additional absorption peak at 345-355 nm which is attributed to the π-π* transition. This is likely favored by the planar orientation enforced by the intramolecular hydrogen bonding in the coated gold nanoparticles.

In addition to the slight absorption band shift, the coated gold nanoparticle composite experiences the elimination of the phenol (—OH) group and the formation a new —ON— donor group, which is a hybrid of imino nitrogen of the amine group and oxygen of the phenol ring (see Formula 2). The —ON— group is formed by the strong tendency of deprotonation of the phenol moiety during formation of the gold nanoparticle composite.

The —ON— donor group in the gold nanoparticle composite serves as a high selectivity and high affinity receptor for Fe(III) ions. Upon contact and binding of the paramagnetic ferric ions to the —ON— group, quenching of fluorescent emission occurs due to chelation enhanced quenching, generating a fluorescent signal as the plasmonic absorption peak shifts from 530-240 to 555-565 nm, preferably 556-562 nm, more preferably 557-560 nm. The fluorescent signal is manifested as a quench or reduction in fluorescent emission at 490-495 nm, for example, at 491 nm. The gold nanoparticle core acts as a carrier and a signaling unit while the bidentate, thiolated Schiff base ligands as hosts for the Fe(III) ions. The binding of Fe(III) ions to the gold nanoparticle composite also results in aggregation.

The Schiff base coated gold nanoparticle composite of the present disclosure has a 1:1 binding mode for Fe(III) ions per ligand that is present in the nanoparticle composite, with a binding constant of $8.2-8.7\times10^5$ $M^{-1}$ as calculated from absorption titration and $2.5-3.0\times10^5$ $M^{-1}$ as calculated from emission titration Another embodiment of the disclosure relates to a method of detecting and quantifying ferric ions in a fluid sample. The fluid sample may be an inorganic sample such as but not limited industrial effluent water and tap water or a biological sample such as but not limited to blood and blood plasma. The fluid sample is an aqueous sample comprising 10-100% v/v of water as the solvent. In certain embodiments, the fluid sample may further comprise up to 90% v/v of an organic solvent such as ethanol as a secondary solvent. The fluid sample may comprise 5-90% v/v of ethanol, preferably 10-90%, 20-90%, 30-90% or 40-90%, more preferably 50-90% or 60-90%, even more preferably 75-90% or 80-90%. In one embodiment, the fluid sample comprises 90% v/v of ethanol and 10% v/v of water.

The method of detecting and quantifying Fe(III) ions may be executed in batch mode or fixed mode (column mode). For the batch mode, the Schiff base ligand functionalized gold nanoparticle composite is added and dispersed into a fluid sample at a concentration of 5-50 μM, preferably 5-25 μM, more preferably 5-15 μM. In one embodiment, the concentration of the gold nanoparticle composite in a tested fluid sample is 10 μM. The fluorescence signal at 556-562 nm is then measured spectrophotometrically. In the fixed mode, the gold nanoparticle composite is affixed to a substrate (e.g. plate, column) which is then immersed in a fluid sample at the above-described concentration ranges.

In one or more embodiments, the Fe(III) fluorescent detection method may further include and be preceded by calibration procedures with a series of known amounts of Fe(III) ions in the same medium as the tested fluid sample, in order to obtain a calibration curve.

The detection method provided herein has a Fe(III) detection limit of 0.8-2.0 μM without interference from one or more of other metal ions, preferably 1.0-1.5 μM, more preferably 1.1-1.3 μM. In some embodiments, the one or more of other metal ions are selected from the group consisting of Al(III), Ni(II), Cu(II), Co(II), Hg(II), Zn(II), Na, K, Ca(II) and Rb.

As the binding of Fe(III) ions to the functionalized gold nanoparticle composite leads to aggregation of the formed complex, the method can also be used to effectively remove Fe(III) ions from the fluid sample.

The following examples further illustrate protocols for preparing and characterizing gold nanoparticles coated with (E)-2-(((4-mercaptophenyl)imino)methyl) phenol ligands, and are not intended to narrow the scope of the appended claims.

EXAMPLE 1

Synthesis of Schiff Base Ligands

The synthesis reactions (of both Schiff-base ligands and Schiff base coated gold nanoparticles) were carried out under argon atmosphere using a standard Schlenk technique. All the chemicals and solvents were purchased from Sigma-Aldrich. The $^1H$ and $^{13}C$ NMR spectra and chemical shifts were recorded in deuterated Chloroform ($CDCl_3$) recorded on a JEOL 500 MHz spectrometer. Chromatograms were recorded using autosampler of a Shimadzu GC-MS (EI-MS) interfaced with a quadrupole ion trap detector by injecting samples into the GC injection port. FT-IR spectra were collected on Nicolet (Thermo Scientific) using iTR as sample holder in the wave number range of 600 to 4000 $cm^{-1}$. Absorption spectra were collected at room temperature in the 4000-400 $cm^{-1}$ using JASCO-670 spectrophotometer and emission spectra on the Fluorolog (Horiba) system. Transmission Electron Microscopy (TEM) were carried out on Philips CM200 operated at 200 kV by spreading one drop of the aqueous Schiff-base ligand gold nanoparticle solution on the carbon coated copper 200 mesh grid and allowing to dry at room temperature.

The thiolated bidentate Schiff-base ligands [(E)-2-(((4-mercaptophenyl)imino)methyl) phenol) were prepared according to the procedure of FIG. 1 and as reported in the literature [F. Tisato, F. Refosco, U. Mazzi, G. Bandoli and M. Nicolini, J. Chem. Soc., Dalton Trans., 1987, 1693; K. C. Grabar, R. G. Freeman, M. B. Hommer, M. J. Natan, Anal. Chem. 1995, 67, 735—each incorporated herein by reference in its entirety]. To an ethanolic solution of salicylaldehyde, an equimolar amount of 4-aminothiphenol was added refluxed at 90° C. for 5 h. The yellow precipitate was filtered, purified by recrystallization in methanol and finally dried in vacuum. The yellow solid was recrystallized from methanol with 94% yield. Formation of an imino-containing ligand was confirmed by $^1H$ and $^{13}C$ NMR which showed the characteristic olephenic proton shift at 67.4 ppm, supported by the olephenic carbon shift at δ160.2 ppm. The FT-IR spectrum of imino ligand showed peaks at 1613 $cm^{-1}$ and 3448 $cm^{-1}$, corresponding to the vibration mode of C=N and —H group of salicylaldehyde.

EXAMPLE 2

Synthesis of Gold Nanoparticles Coated with Schiff Base Ligands

Figure 2:
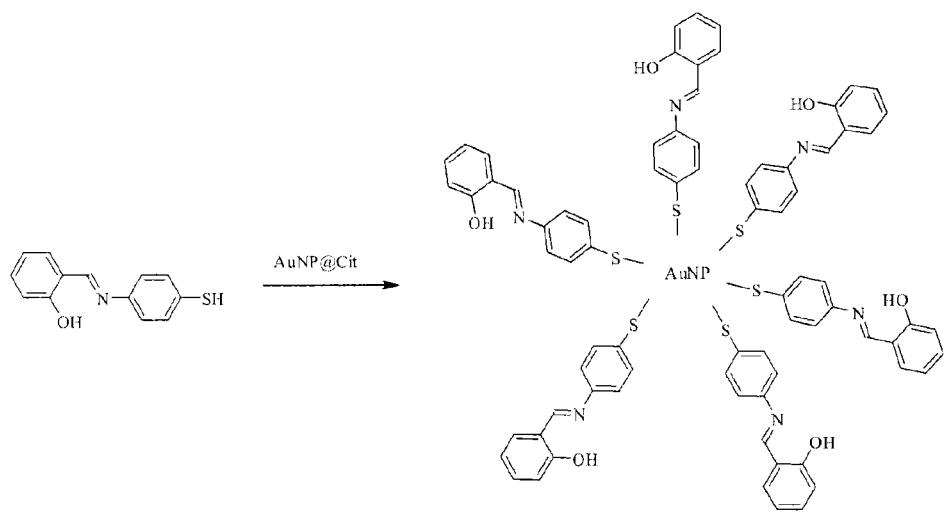
FIG. 2 is a schematic diagram illustrating the synthesis of gold nanoparticles coated with (E)-2-(((4-mercaptophenyl)imino)methyl) phenol ligands by a citrate reduction method.

Gold nanoparticles coated with citrate were prepared by citrate reduction method in deionized water as shown in FIG. 2. $HAuCl_4.3H_2O$ (0.33 g, 1 mmol) in 500 ml water was refluxed a 1 L round bottom flask equipped with a condenser, with vigorous stirring under argon for 30 min. 10 ml of trisodium citrate (1.14 g, 3.88 mmol) solution was added rapidly with color changing from yellow to purple. After boiling for 10 more min, the heating mantle was removed but stirring was continued for another 10 min. The gold nanoparticles coated with Schiff base ligands were prepared as follows: To the freshly prepared citrate coated gold nanoparticles (50 ml), Schiff-base in minimal methanol medium (5 mg in 0.5 ml methanol) was added and stirred for 5 h. Optimization of the gold to ligand molar ratio is crucial for the preparation of the Schiff base coated gold nanoparticles, since excess of ligand leads to aggregation and precipitation. The Schiff base coated gold nanoparticles precipitated upon adding an equal amount of acetone and stirring the solution for 4 h. The nanoparticles were collected by centrifugation and washed successively with water and acetone.

Figure 3A:
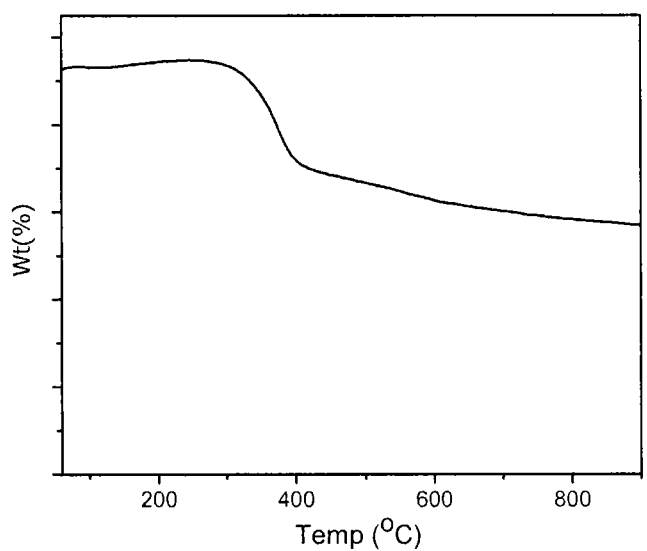
FIG. 3A is a thermogravimetric analysis (TGA) curve of gold nanoparticles coated with (E)-2-(((4-mercaptophenyl)imino)methyl) phenol ligands.
Figure 3B:
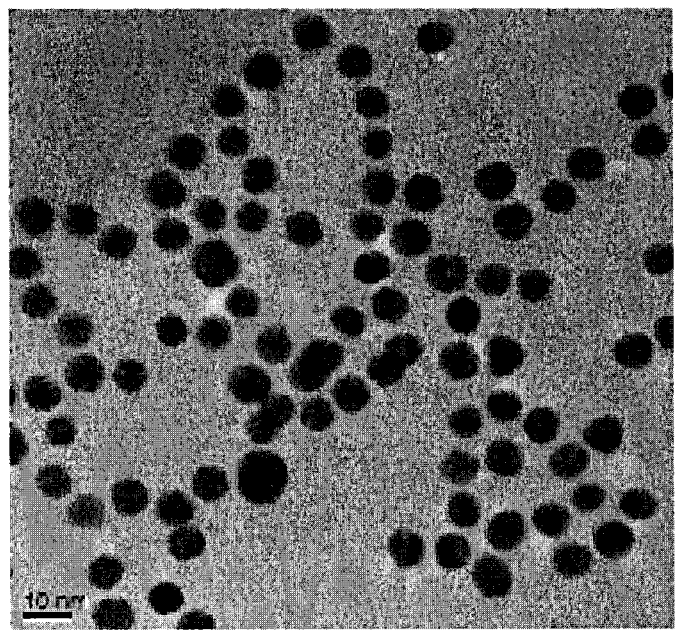
FIG. 3B is a transmission electron microscopy (TEM) image of gold nanoparticles coated with (E)-2-(((4-mercaptophenyl)imino)methyl) phenol thiolated Schiff base ligands.

The formation of a homogeneous monolayer of (E)-2-(((4-mercaptophenyl)imino)methyl) phenol ligands (which is purple in color) coating the gold nanoparticles was confirmed by analytical and spectroscopic techniques For instance, visible absorption spectra showed the absorption band shift ($\lambda_{max}$) at 525 nm for the citrate coated nanoparticles to 530 nm for the ligand modified moieties. The observed shift could be attributed to the surface plasmon vibration in the latter. The binding of thiolated-imino ligand to gold surface was further confirmed by the disappearance of —SH stretching in FT-IR, indicating Au—S bond formation [K. Pomazal, C. Prohaska, I. Steffan, G. Reich, J. F. K. Huber, Analyst, 1999, 124, 657; C. A. Mirkin, R. L. Letsinger, R. C. Mucic, J. J. Storhoff, Nature 382 (1996) 607-609; M.-C. Daniel, D. Astruc, Chem. Rev. 104 (2004) 293-346—each incorporated herein by reference in its entirety]. The diffraction peaks at $2\theta=38.2$, 44.4, 64.5, 77.5 and 81.7 correspond respectively to (111), (200), (220), (311) and (222) planes in gold nanoparticles [C. Burda, X. Chen, R. Narayanan, M. A. El-Sayed, Chem. Rev. 105 (2005) 1025-1102—incorporated herein by reference in its entirety]. The TEM image of FIG. 3B shows uniformly distributed spherical particles with an average diameter of 8-10 nm. A high loading of Schiff-base ligand was confirmed from thermogravimetric analysis which showed 21.5% weight loss in the temperature range of 200-800° C. (ramp rate: 10°/min.), corresponding to the decomposition of the organic ligand (see FIG. 3A).

EXAMPLE 3

Figure 4:
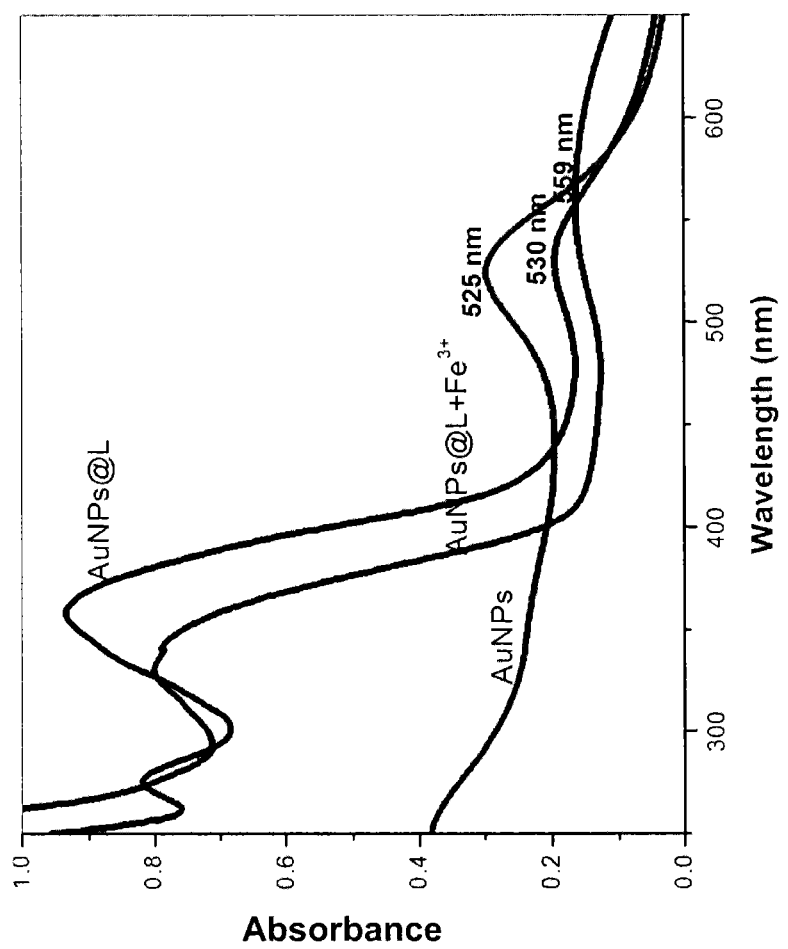
FIG. 4 shows UV-Vis absorption spectra of gold nanoparticles coated with citrate ligands, free (E)-2-(((4-mercaptophenyl)imino)methyl) phenol ligands and (E)-2-(((4-mercaptophenyl)imino)methyl) phenol ligands that are bonded to Fe(III) ions.

Fe(III) Selectivity of Gold Nanoparticles Coated with (E)-2-(((4-Mercaptophenyl)imino)methyl) Phenol Ligands Preliminary results of UV-Vis absorption and fluorescent emission studies revealed that the synthesized gold nanoparticles exhibit selectivity toward ferric ions with concentration of $1\times10^{-5}$ mmol/mL in a 9:1 ethanol/water system. As seen from FIG. 4, in the absence of ligand, peak at 525 nm corresponds to the surface plasma resonance (SPR) of gold nanoparticles. On attachment of the (E)-2-(((4-mercaptophenyl)imino)methyl) phenol ligand, there is a red shift to 530 nm. Moreover, there is an additional absorption band at 350 nm which is attributed to the $\pi$-$\pi$* transition. This is likely favored by the planar orientation enforced by the intramolecular hydrogen bonding in the coated gold nanoparticles [Keck, J.; Kramer, Horst E. A.; Port, H.; Hirsch, T.; Fischer, Peter.; Rytz, G. *J. Phys. Chem.* 1996, 100, 14468—incorporated herein by reference in its entirety]. Addition of $Fe^{3+}$ causes the plasmonic absorption peak to shift again from 530 to 559 nm.

Figure 5:
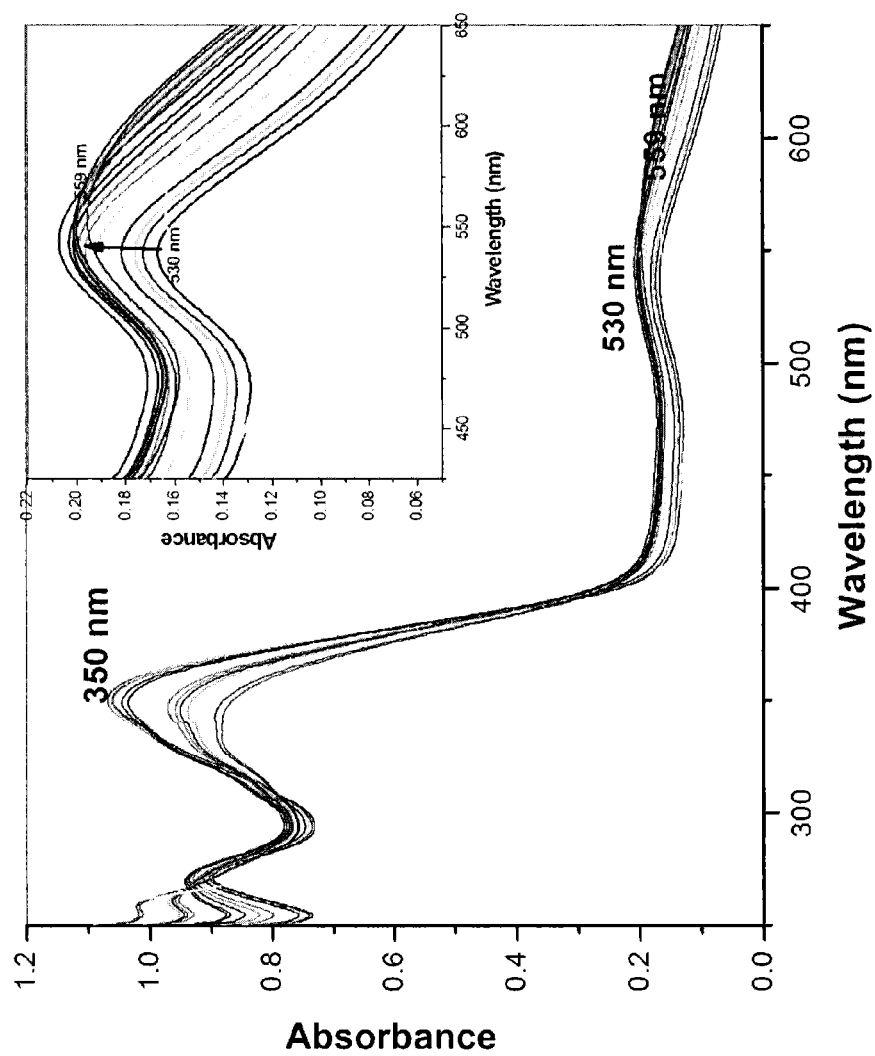
FIG. 5 shows changes in UV-Vis absorption spectra of gold nanoparticles coated with (E)-2-(((4-mercaptophenyl)imino)methyl) phenol ligands upon addition of 10 μM Fe(NO$_3$)$_3$ in 90% v/v ethanol aqueous solution. The inset is an exploded view of the plasmonic absorption peak shift from 530 to 559 nm upon increasing Fe(III) concentration.
Figure 7:
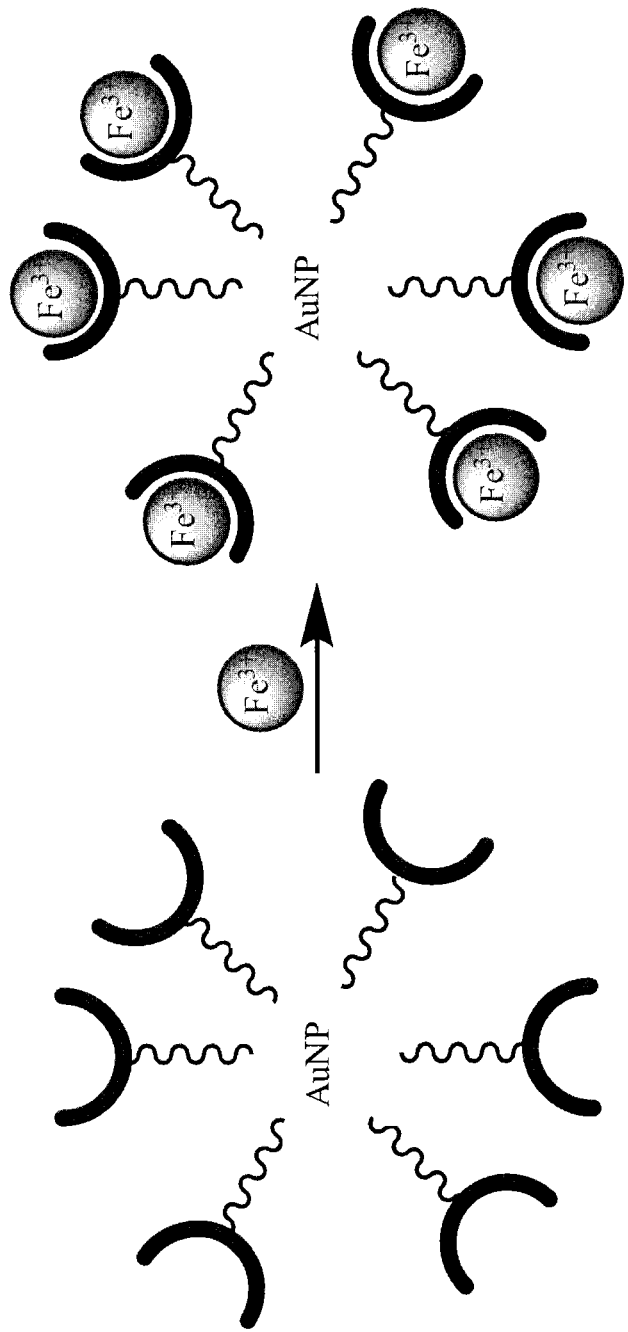
FIG. 7 illustrates the Fe(III) binding mechanism of the Schiff base coated gold nanoparticles according to one embodiment.

Other metal ions did not influence the UV-Vis signature, indicating that no aggregation occurred, akin to that observed with ferric ions. However, upon further ingress of ferric ions in solution containing the coated gold nanoparticles, the absorption band at 350 nm is gradually but systematically quenched while that at 530 nm is shifted to 559 nm synchronously, as shown in FIG. 5. The 530 nm to 559 nm shift in the plasmonic absorption band up on gradual increase in Fe(III) concentration shows cation-induced aggregation of gold nanoparticles. The shift in the peak is linear up to 1 equivalent of Fe(III) (see inset of FIG. 5), indicating the formation of a 1:1 complex with a strong affinity (binding constant: $8.5\times10^5$ $M^{-1}$; estimated error$\leq$10%) [Connors, K. A. *Binding Constants: the Measurement of Molecular Complex Stability*. New York: Wiley, 1987; pp 21-101; 339-343; Thordarson, P. *Chem. Soc. Rev.* 20—each incorporated herein by reference in its entirety]. A scheme illustrating the Fe(III) binding mechanism of the Schiff base coated gold nanoparticles is provided in FIG. 7.

Figure 6:
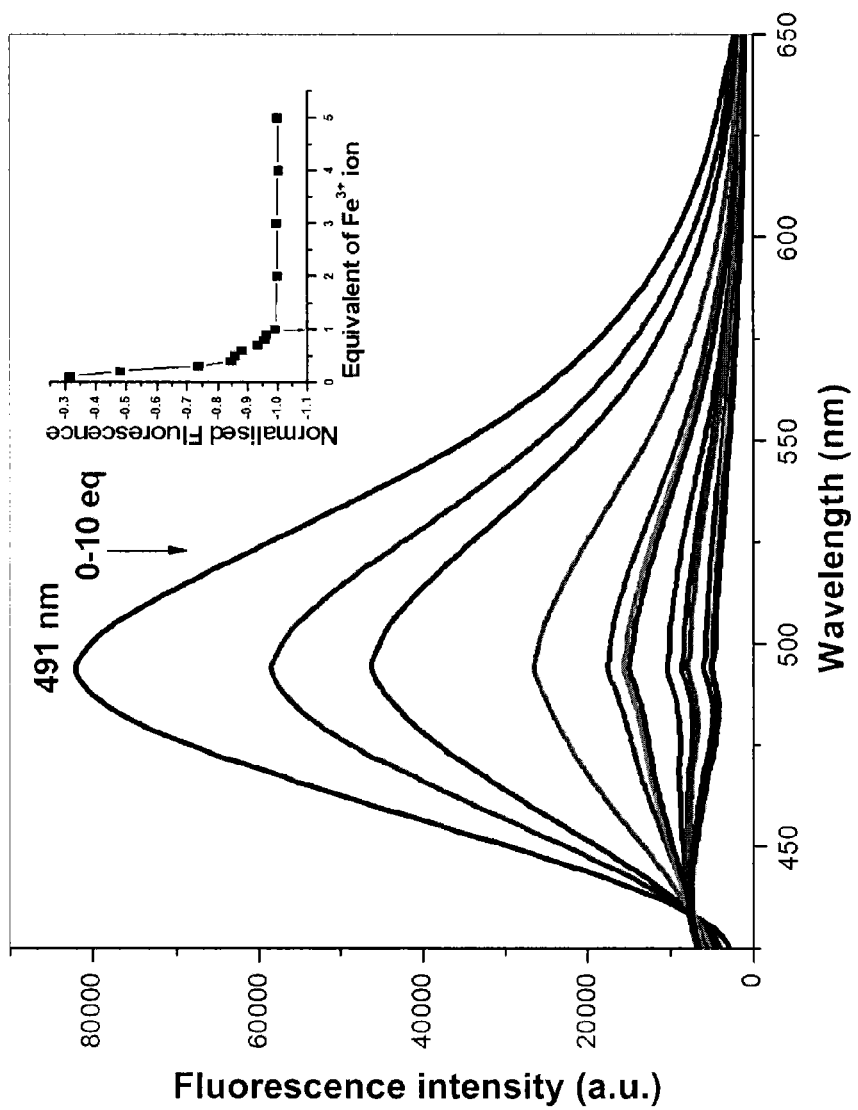
FIG. 6 shows the fluorescence titration of 10 μM gold nanoparticles coated with (E)-2-(((4-mercaptophenyl)imino)methyl) phenol ligands in 90% v/v ethanol aqueous solution at $\lambda_{ex}$=390 nm. The inset shows a mole ratio plot of emission at 491 nm.

The results of photoluminescence studies of the synthesized gold nanoparticles with iron (concentration=10 μM) in 90% (v/v) ethanol aqueous solution are shown in FIG. 6. The emission peak at 491 nm on excitation with 390 nm radiation is due to the intramolecular charge transfer (ICT) between the amino and phenolic groups of the ligand in the gold nanoparticles. Addition of ferric ions causes quenching of fluorescent emission due to chelation enhanced quenching (CEQ). This is due to the fact that Fe (III) is paramagnetic. The quenching in the presence of iron provides a very fast and efficient non-radiative decay of the excited states due to the electron or energy transfer between cations and the ligand. The binding constant, as calculated from emission titration, is $2.9\times10^5$ $M^{-1}$.

EXAMPLE 4

Competition with Other Metal Ions

Figure 8:
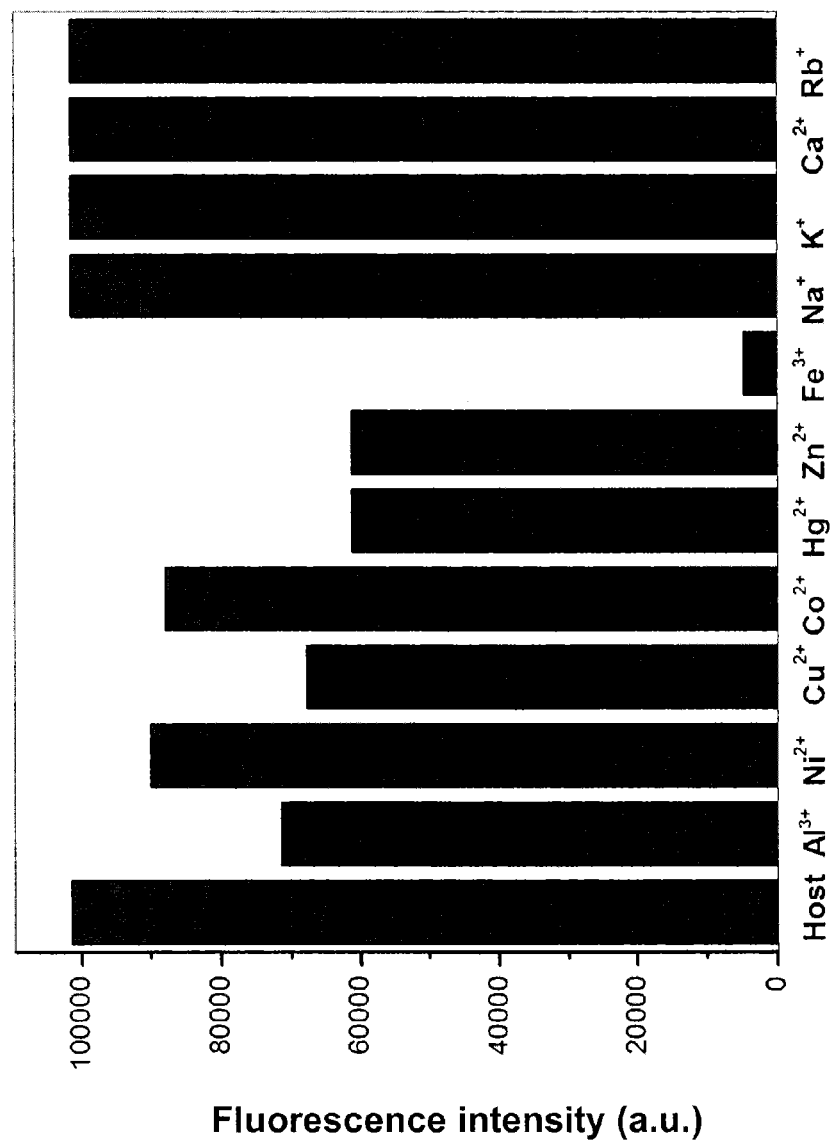
FIG. 8 illustrates the metal ion selectivity of gold nanoparticles coated with (E)-2-(((4-mercaptophenyl)imino) methyl) phenol ligands. Bars indicate the fluorescence intensity (excitation at 390 nm and emission at 491 nm).

The selectivity and tolerance of the thiolated Schiff base ligand coated gold nanoparticles of the present disclosure for Fe(III) over other cations was investigated by adding 10 equivalent of respective metal ions to 10 μM of the gold nanoparticle solution. There was partial quenching in case of Al(III), Cu(II), Hg(II), and Zn(II) as shown in FIG. 8, whereas the molecular fluorescence is quenched to a maximum level in the case of Fe(III), thereby imparting the highest sensitivity towards ferric ion detection by the gold nanoparticles. This could be attributed to the difference in the coordinative interaction energy for various cations which otherwise do not differ much in their ionic size. Thus, this can be exploited for discriminative purposes, especially for fluorescent sensing [Fabbrizzi, L.; Licchelli, M.; Pallavicini, P.; Parodi, L.; Taglietti, A. In *Transition Metals in Supramolecular Chemistry*; Sauvage, J. P., Ed. Fluorescent sensors for and with transition metals; John Wiley & Sons Ltd: Chichester, 1999—incorporated herein by reference in its entirety]. Fe(III) has high thermodynamic affinity for —ON— group, which is a hybrid of imino nitrogen of the amine and oxygen of the phenol ring. The —ON— group is formed by the strong tendency of deprotonation of phenol during complex formation, with fast metal-to-ligand binding kinetics which otherwise is not possible with other transition metal ions. The estimated detection limit of the thiolated Schiff base ligand coated gold nanoparticles is 1.2 µM of Fe(III) without interference from other metal ions.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A fluorescent gold nanoparticle composite, comprising:
   a gold nanoparticle core; and
   a ligand monolayer surrounding the gold nanoparticle core;
   wherein the ligand monolayer comprises a plurality of substituted or unsubstituted (E)-2-(((4-mercaptophenyl)imino)methyl) phenol units that are bound to the gold nanoparticle core through a sulfur atom.

2. The fluorescent gold nanoparticle composite of claim 1, wherein the ligand monolayer comprises 2-12 of (E)-2-(((4-mercaptophenyl)imino)methyl) phenol units.

3. The fluorescent gold nanoparticle composite of claim 1, having a spherical shape and an average diameter of 7-15 nm.

4. The fluorescent gold nanoparticle composite of claim 1, wherein more than 75% of the fluorescent gold nanoparticle composites have a diameter of 8-10 nm.

5. The fluorescent gold nanoparticle composite of claim 1, wherein each of the plurality of (E)-2-(((4-mercaptophenyl)imino)methyl) phenol units comprises an —ON— electron donor group.

6. The fluorescent gold nanoparticle composite of claim 5, wherein the —ON— electron donor group is formed by an imino nitrogen of an amine group of the (E)-2-(((4-mercaptophenyl)imino)methyl) phenol unit and an oxygen of a deprotonated phenol ring of the (E)-2-(((4-mercaptophenyl)imino)methyl) phenol unit.

7. The fluorescent gold nanoparticle composite of claim 1, having two plasmonic absorption peaks at 345-355 nm and 530-540 nm.

8. The fluorescent gold nanoparticle composite of claim 1, wherein, upon binding with one or more Fe(III) ions, a fluorescence signal emits at 490-495 nm and a plasmonic absorption peak shifts from 530-540 nm to 555-565 nm.

9. The fluorescent gold nanoparticle composite of claim 1, having a Fe(III) binding constant of $8.2\text{-}8.7 \times 10^5$ $M^{-1}$ as calculated from absorption titration.

10. The fluorescent gold nanoparticle composite of claim 1, having a Fe(III) binding constant of $2.5\text{-}3.0 \times 10^5$ $M^{-1}$ as calculated from emission titration.

11. A method for detecting and quantifying Fe(III) ions in a fluid sample, comprising:
    contacting the fluid sample with the fluorescent gold nanoparticle composite of claim 1; and
    measuring fluorescence emission at 490-495 nm to determine an Fe(III) concentration in the fluid sample;
    wherein during the contacting, the fluorescent gold nanoparticle composite selectively binds to the Fe(III) ions at a Fe(III)/(E)-2-(((4-mercaptophenyl)imino)methyl) phenol molar ratio of 1:1, causing a reduction in the fluorescence emission.

12. The method of claim 11, wherein the selective binding of the fluorescent gold nanoparticle composite to the Fe(III) ions further causes a shift in a plasmonic absorption peak from 530-540 nm to 555-565 nm.

13. The method of claim 11, wherein the selective binding of the fluorescent gold nanoparticle composite to the Fe(III) ions further results in formation of an aggregate.

14. The method of claim 11, further comprising measuring the fluorescence emission of a plurality of calibration samples to obtain a calibration curve, the plurality of calibration samples comprising different, known amounts of Fe(III) ions.

15. The method of claim 11, wherein the method is executed in batch mode or fixed mode.

16. The method of claim 11, wherein the fluorescent gold nanoparticle composite is present at a concentration of 5-25 µM.

17. The method of claim 11, having a Fe(III) detection limit of 1.0-1.5 µM without interference from one or more of other metal ions.

18. The method of claim 17, wherein the one or more of other metal ions are selected from the group consisting of Al(III), Ni(II), Cu(II), Co(II), Hg(II), Zn(II), Na(I), K(I), Ca(II) and Rb(I).

19. The method of claim 11, wherein the fluid sample comprises 10-100% v/v of water as a solvent.

\* \* \* \* \*